(12) United States Patent
Stevrin et al.

(10) Patent No.: US 8,928,746 B1
(45) Date of Patent: Jan. 6, 2015

(54) ENDOSCOPE HAVING DISPOSABLE ILLUMINATION AND CAMERA MODULE

(71) Applicants: Peter Magnus Stevrin, Kallinge (SE); Siamak Khatabi, Färjestaden (SE)

(72) Inventors: Peter Magnus Stevrin, Kallinge (SE); Siamak Khatabi, Färjestaden (SE)

(73) Assignee: Stevrin & Partners, Kallinge (SE)

( * ) Notice: Subject to any disclaimer, the term of this patent is extended or adjusted under 35 U.S.C. 154(b) by 0 days.

(21) Appl. No.: 14/058,036

(22) Filed: Oct. 18, 2013

(51) Int. Cl.
*A61B 1/04* (2006.01)
*A61B 1/06* (2006.01)
*H04N 5/235* (2006.01)

(52) U.S. Cl.
CPC .................................. *H04N 5/2354* (2013.01)
USPC .............................. 348/68; 600/109; 600/160

(58) Field of Classification Search
None
See application file for complete search history.

(56) References Cited

U.S. PATENT DOCUMENTS

| | | | |
|---|---|---|---|
| 5,087,112 A * | 2/1992 | Feinbloom | 359/800 |
| 5,220,400 A * | 6/1993 | Anderson et al. | 356/240.1 |
| 5,394,865 A | 3/1995 | Salerno | |
| 6,117,071 A | 9/2000 | Ito et al. | |
| 8,484,966 B2 | 7/2013 | Rasmussen et al. | |
| 2003/0171652 A1 * | 9/2003 | Yokoi et al. | 600/160 |
| 2007/0049794 A1 | 3/2007 | Glassenberg et al. | |
| 2007/0162095 A1 | 7/2007 | Kimmel et al. | |
| 2007/0172230 A1 * | 7/2007 | Wernersson | 396/439 |
| 2010/0002312 A1 * | 1/2010 | Duparre et al. | 359/741 |
| 2010/0295077 A1 * | 11/2010 | Melman | 257/98 |
| 2010/0298640 A1 * | 11/2010 | Oneda et al. | 600/109 |
| 2011/0109232 A1 * | 5/2011 | Schulz et al. | 315/151 |
| 2011/0115882 A1 * | 5/2011 | Shahinian et al. | 348/45 |
| 2013/0127980 A1 * | 5/2013 | Haddick et al. | 348/14.08 |
| 2013/0137923 A1 * | 5/2013 | Honda et al. | 600/109 |
| 2013/0170206 A1 * | 7/2013 | Isogai et al. | 362/235 |

* cited by examiner

*Primary Examiner* — Frederick Bailey
(74) *Attorney, Agent, or Firm* — Foley & Lardner LLP; Christopher C. Bolten; Nicola A. Pisano

(57) ABSTRACT

An endoscope having a single-use disposable illumination and camera module is provided in which an imaging element is disposed within an annular tube of optically transparent material having proximal and distal ends, wherein the proximal end is configured to engage a plurality of LEDS and the distal end has a cross-section in the form of an arc of a circle or ellipse, so that the annular tube serves as a light mixer and diffuser, providing uniform illumination within the field of view of the imaging element. Methods of analyzing and displaying the output of the endoscope also are provided.

20 Claims, 4 Drawing Sheets

ENDOSCOPE HAVING DISPOSABLE ILLUMINATION AND CAMERA MODULE

FIELD OF THE INVENTION

The present invention generally pertains to apparatus and a method for diagnostic or therapeutic imaging within a body lumen using an endoscope having a low cost, disposable illumination and camera module.

BACKGROUND OF THE INVENTION

Proper treatment and diagnosis of a patient often involves a thorough examination or internal organs and structures. To conduct an examination, a clinician often uses a visualization device to probe ducts, orifices, bodily openings, or other spaces. One such device is an endoscope, typically constructed of a long thin probe that employs optical fibers to transmit images of interior bodily structures. Previously-known endoscopes suffer a number of disadvantages, including initial capital cost, limited upgradeability to take advantage of improving camera technology, limited illumination capability, and the need for sterilization after each use.

Previously-known endoscopes typically have similar design based on the parts used and placement of these parts. A basic design may include no illumination, which is then added to capture images under low-light conditions. Fiber optics often are used to transmit light to the distal end of low profile endoscopes, although the illumination typically comes from a separate and rather large box with the light source. For example, U.S. Pat. No. 5,394,865 to Salerno describes an endoscope that utilizes fiber optic cables to transmit light to the distal end of the device to illuminate the work area. This device is designed to be reused and sanitized in an autoclave. Such sterilization procedures are time consuming and expensive, and inherently present a non-negligible risk of contamination and infection. Accordingly, it is desirable to provide an endoscope that does not require sterilization by autoclave after use.

U.S. Pat. No. 6,117,071 to Ito, et al. describes an endoscope having a CCD located in an imaging unit near its distal end to gather images. In addition to requiring sterilization after each use, the device described in Ito also has a relatively large insertion profile, i.e., cross sectional area, that limits its use to correspondingly large openings. U.S. Patent Application Publication No. US 2007/0162095 to Kimmel et al. describes a modular visualization stylet that overcomes certain of the disadvantages of prior art devices such as described in Ito, but such devices have not achieved commercial success.

A key drawback inherent in previously-known endoscopes, particularly low-cost disposable endoscopes, is the inability to provide bright, uniform illumination at the work area, irrespective whether the illumination is conducted to the distal end of the endoscope by a light fiber or generated nearer to the distal end of the device using light-emitting diode ("LED") technology. For example, U.S. Pat. No. 8,484,966 to Robertson describes an endoscope having a monolithic distal tip that encases an illumination source consisting of either the distal end of a light fiber or one or more LEDs. In view of the domed shape of the distal tip of the device described in Robertson and the location of the light fiber tips or LEDs, the Robertson device is not expected to provide uniform illumination at of the work area.

Likewise, U.S. Patent Application Publication No. US 2007/0162095 to Glassenberg et al. describes a modular visualization stylet in which an imaging element is disposed within a tubular member with a plurality of LEDs disposed in an annular array around the imaging element. This design also is expected to provide uneven lighting at the work area due to variations in the intensity of the LED lighting.

In view of the drawbacks of previously-known endoscopes, it would be desirable to provide an endoscope having a low cost, disposable illumination and camera module that provides uniform lighting in the field of view of the imaging system.

It further would be desirable to provide an endoscope having a low cost, disposable illumination and camera module that permits easier upgradeability and integration with improvements in camera technology, while preserving the capital investment in reusable portions of the endoscope system.

SUMMARY OF THE INVENTION

To overcome the foregoing drawbacks of previously-known endoscopes, endoscopes constructed in accordance with the principles of the present invention include low-cost, single-use illumination and camera modules. In accordance with one aspect of the invention, the illumination and camera module comprises an imaging element and an annular tube of optically transparent material having proximal and distal ends disposed around the imaging element, wherein the proximal end is configured to engage a plurality of LEDS and the distal end has a curved cross-section. In particular, in some preferred embodiments, a cross-section of the annular tube may be in the form of an arc of a circle or an ellipse. In this manner, the annular tube serves as a light mixer and diffuser, providing uniform illumination within the field of view of the imaging element. The illumination and camera module is configured for single use, and therefore does not require sterilization except after initial manufacture.

In accordance with another aspect to invention, different imaging elements selectably may be disposed within the annular tube. In this manner, an endoscope may be readily upgraded to take advantage of advances in camera design while preserving the physician or hospital's capital investment in reusable portions of the endoscope system. The annular tube of the illumination and camera module may comprise a reflector material, such as silver paint, disposed on the interior surface of the annular tube, to reduce light absorption within the annular tube while shielding the imaging element from light transmitted through the annular tube.

In accordance with yet a further aspect of the invention, the camera and lens elements disposed within the annular tube of the illumination and camera module optionally may be removed to permit replacement with a lens having a different magnification. To avoid unnecessary material cost and to preserve storage space, the illumination and camera components may comprise individual modules that are packaged separately in sterile containers. In this case, a physician need only select the illumination and camera components intended to be used at a particular time and assemble them at the time of use, thereby enabling the physician to customize the endoscope as may be appropriate and desired for a specific patient and application.

The disposable endoscope of the present invention also may be constructed so that the illumination and camera module is detachably connected to reusable electronics via a thin cable, so that only the illumination and camera module and cable are discarded after a single use. In one embodiment, the illumination and camera module comprises an approximately cylindrical capsule having a length of about 6 mm and a diameter of about 3 mm, while the cable has a diameter of about 1.6 mm. In this case, the illumination and camera module may advantageously be swallowed to capture images of the esophagus, stomach or respiratory tract without sedation.

Methods of assembling and using the endoscope of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference numerals refer to like parts throughout, and in which.

DETAILED DESCRIPTION OF THE INVENTION

Figure 1:
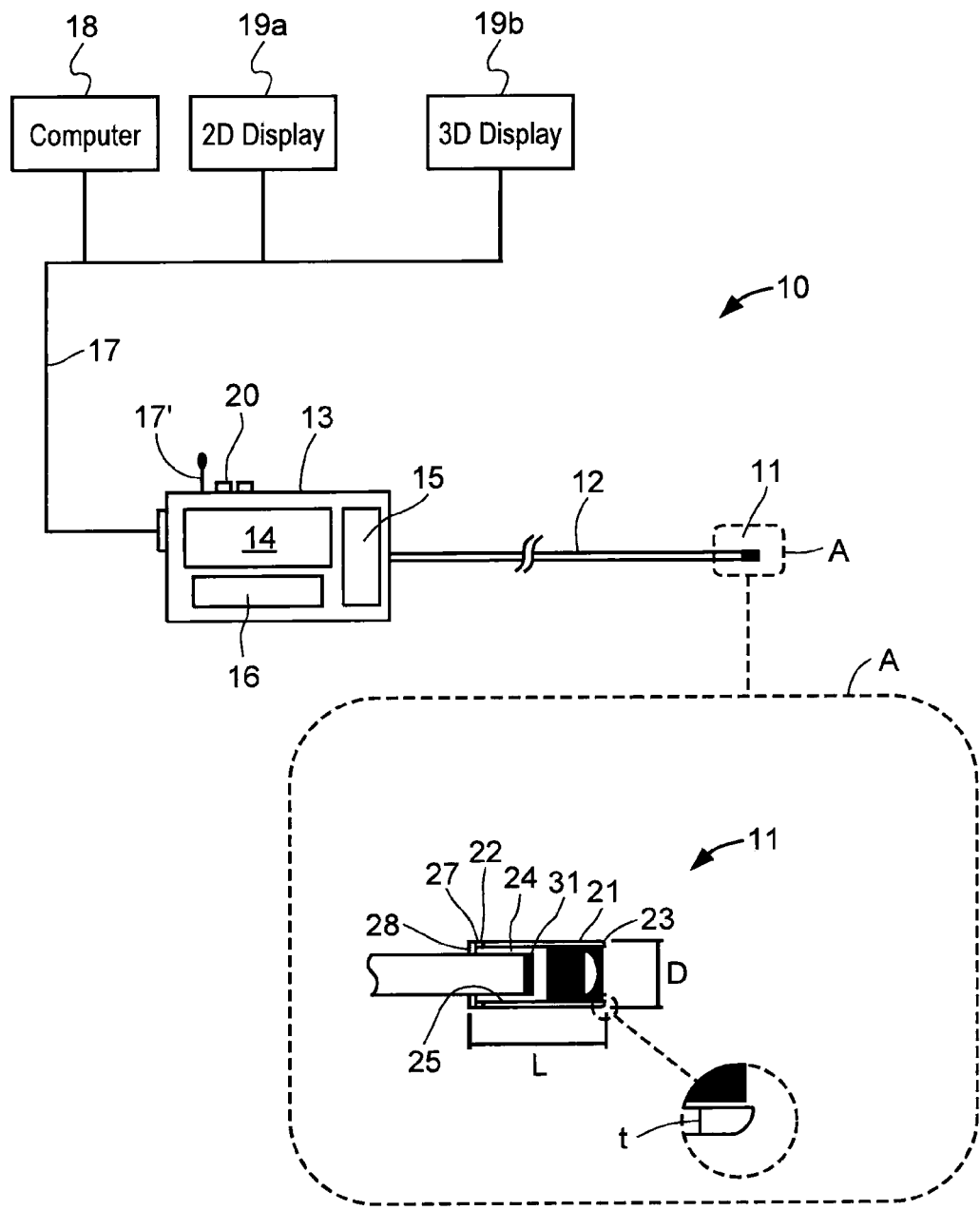
FIG. 1 is a schematic view of an illustrative embodiment of an endoscope constructed in accordance with the principles of the present invention.

The present invention is directed to an endoscope having a low-cost, single use, disposable illumination and camera module that provides uniform illumination of the work area within the field of view of the camera. Following use, the illumination and camera module and cable that has been inserted into a patient or otherwise contaminated may be discarded, while reusable components of the endoscope system remain available for future use.

In accordance with an embodiment containing a single forward-facing image sensor, the disposable illumination and camera module is externally powered, has an approximately cylindrical shape, with a diameter of about 3.0 mm and a length of between about 3.0 mm and 6.0 mm. The module is coupled to a thin flexible cable that includes a first subset of wires to power the image sensor and LEDs, and a second subset of wires that carry the output signals of the imaging element to the image processor and display. The imaging element may comprise a high resolution CMOS sensor, such as are commonly used in smartphone cameras and medical systems, providing an extremely robust and low-cost imaging system.

In an alternative embodiment, two image sensors may be placed in a side-by-side forward-facing orientation to provide a stereoscopic view, for which the illumination and camera module has an approximately cylindrical shape with a diameter of about 5.0 mm and a length of between about 3.0 mm and 6.0 mm. In another embodiment, three image sensors may be placed in a side-by-side forward-facing or lateral-facing configuration and the resulting images seamlessly integrated to provide a 180 degree image from an illumination and camera module having an approximately cylindrical shape, a diameter of about 10.0 mm and a length of between about 3.0 mm and 6.0 mm. In still other embodiments, four or more image sensors may be placed in a side-by-side lateral-facing configuration and the resulting images seamlessly integrated to provide a 360 degree image from an illumination and camera module having an approximately cylindrical shape, a diameter of about 14.0 mm.

In alternative embodiments, the illumination and camera module may be disposed on a thin, flexible cable, e.g., 1.6 mm in diameter, that permits the distal end of the endoscope to be readily swallowed by the patient, without sedation, to permit visualization of the alimentary or respiratory tracts. Unlike capsule-type imaging systems for which the physician has no control over the rate of descent of the capsule through the esophagus and into the stomach, the flexible cable provides a tether that enables the physician to closely control descent of the distal end of the endoscope. This in turn permits that physician to examine the body lumen during advancement of the illumination and camera module, enables collection of image data to permit generation and display of two- and three-dimensional images, and enables the physician to readily retrieve the distal end of the endoscope when the examination is completed.

As a further alternative, or in addition, the cable may be selected to provide a sufficiently rigid support to permit the illumination and camera module to be advanced in a distal direction by pushing the housing manipulated by the physician. In this case, the illumination and camera module may be advanced through the urethra to examine, for example, a patient's bladder, and the extremely small size of the illumination and camera module and cable readily would permit such use without sedation or application of local anesthesia.

The illumination and camera module of the endoscope of the present invention optionally also may be configured to permit the imaging element and/or lens to be selected and installed in the illumination and camera module to tailor the functionality of the endoscope as desired by the physician for a specific patient or application.

Referring now to FIG. 1, an exemplary embodiment of endoscope 10 of the present invention is described. Endoscope 10 comprises illumination and camera module 11 disposed at the distal end of thin flexible cable 12. Cable 12 is detachably coupled to housing 13, which illustratively contains, processor board 14, camera board and frame grabber 15 and power source 16, which may be one or more conventional dry-cell disposable batteries or lithium ion rechargeable batteries. Processor board 14 may be coupled by cable 17 to computer 18 for storage and retrieval of images generated by endoscope 10. Alternatively or in addition, computer 18 may be programmed with image processing software that takes as input the image data output by endoscope 10 and generates two- or three-dimensional reconstructions of the body lumen that may be displayed on optional two-dimensional display 19*a* or optional three-dimensional display 19*b*. Housing 13 also may include switches 20 for activating the LEDs and image sensor of the illumination and camera module 11, and for activating frame grabber 15 to create a still image from the video stream output generated by the image sensor.

Alternatively or in addition, housing 13 may include antenna 17' and a wireless chipset, e.g., compliant with the IEEE 802.11 WiFi standards, for wirelessly transmitting the video image generated by endoscope 10 to computer 18 or displays 19*a* or 19*b* without cable 17 as described above. This arrangement may be particularly advantageous for use in a physician's office because it permits the computer and display to be placed outside of the sterile field, while also allowing the physician greater maneuverability during use of endoscope 10.

In one embodiment, regardless whether housing 13 is coupled to computer and a display via cable 17 or antenna 17', cable 12 is configured to detachably couple illumination and camera module 11 to the circuitry within housing 13. In this manner, cable 12 and illumination and camera module 11 may be detached from housing 13 after a single patient use; while housing 13 may be disinfected for subsequent reuse with a new cable and illumination and camera module for a different patient. Cable 12 may serve as a tether, and may include a plurality of scale markings or fiducials that enable a user to measure a distance traveled by the capsule housing into a lumen of a body. Whereas conventional endoscopes employ precision optics and imaging sensors, the availability of low-cost modular imaging system components enables manufacture of the disposable components of the endoscope of the present invention at very low cost. Advantageously, housing 13 of endoscope 10 is expected to be relatively compact, e.g., a rectangular box having a length of 12 cm, width of 12 cm, and depth of 2 cm, thereby enabling it to be placed within a plastic bag to minimize clean-up post examination.

Figure 2:
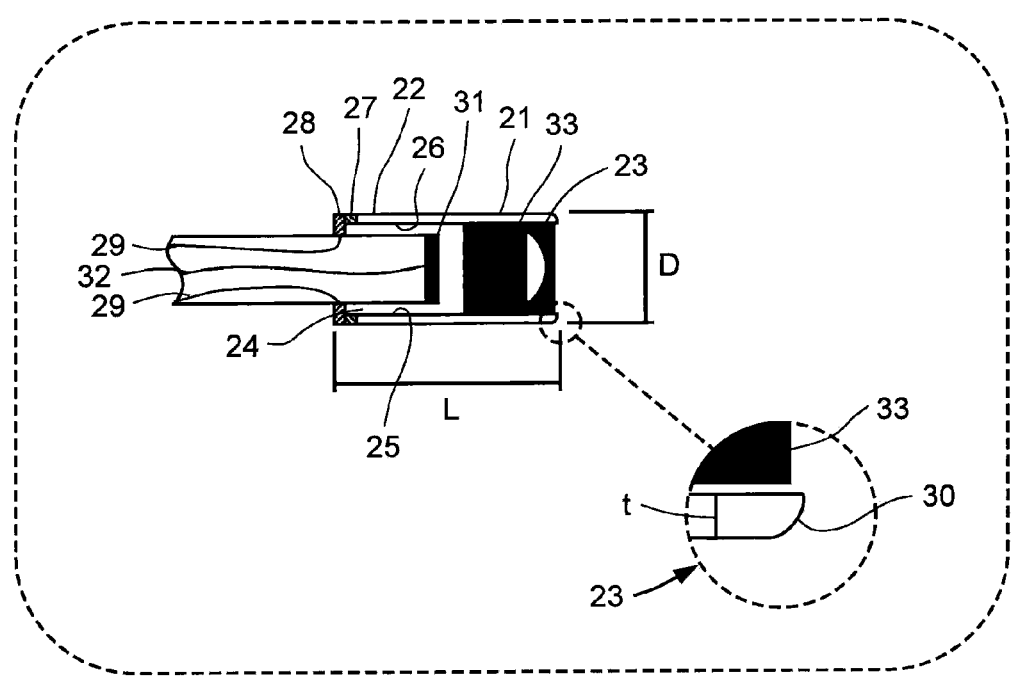
FIG. 2 is an enlarged view of the distal portion of the endoscope of FIG. 1.

Referring now to the inset portion A of FIG. 1 and FIG. 2, the detailed construction of illumination and camera module 11 is described. In the embodiment depicted in FIGS. 1 and 2, illumination and camera module 11 includes a single forward-facing imaging sensor. Other embodiments may contain two, three, four or more image sensors arranged in either a forward-facing or lateral-facing configuration, as described below. Illumination and camera module 11 includes annular optically transparent tube 21 having proximal end 22, distal end 23, annulus 24 and interior surface 25. Preferably, tube 21 comprises an optically transmissive, low absorption material such as glass or polycarbonate and includes a layer of reflective material 26, e.g., silver paint, disposed on both interior surface 25 and the exterior surface of tube 21 to reduce light leakage tube 21. Optionally, layer of reflective material 26 may be omitted by highly polishing the interior and exterior surfaces of tube 21. Polycarbonate is a particularly preferred material for construction of tube 21 because it is optically transparent throughout the entire spectrum of visible light, is a good electrical insulator, and is heat resistant and biocompatible.

Proximal end 22 of tube 21 preferably is configured to contact LEDs 27 so that light emitted by LEDs 27 is conducted into tube 21 with little or no backwards reflection into the LED package. LEDs 27, at least two and more preferably four or more, are spaced equidistant apart around the circumference of tube 21 and mounted on circular printed circuit board 28, which provides power to the LEDs via wires 29 that extend through cable 12. In accordance with one aspect of the present invention, distal end 23 of tube 21 includes curved cross-section 30 that comprises an elliptical or circular arc selected so as to provide uniform illumination at a work site disposed distal to illumination and camera module 11, within the field of view of image sensor 31. In one preferred embodiment, cross-section 30 comprises an approximately quarter-circular arc having a radius substantially equal to thickness t of tube 21, e.g., about 0.25 mm. In another embodiment, for tube 21 having a thickness of 0.25 mm, cross-section 30 may form an arc of an ellipse having a major axis of about 0.27 mm and a minor axis of about 0.1 mm, wherein the major axis is inclined at an angle of about 22.5 degrees from axis of the interior surface of tube 21. It has been observed that by mounting four LEDs 27 spaced equidistant around the circumference at the proximal end of tube 21, where tube 21 has length L of about 6 mm, diameter D of about 3.0 mm, thickness t of about 0.25 mm and reflective coating 26, illumination passing into the proximal end of tube 21 mixes and diffuses, providing substantially uniform illumination when projected through distal end 23 having curved cross-section 30.

Image sensor 31 is mounted on a die coupled to wires 32 that extend through cable 12 to provide power to the image sensor and to transmit the signals generated by image sensor 31 to the circuitry disposed in housing 13. To prevent crosstalk of the illumination provided by LEDs 27 and tube 21 to image sensor 31, interior surface 25 of tube 21 preferably includes light shield 33, which may comprise a thin layer of black paint. Lens 34 is disposed within annulus 24 of illumination and camera module 11 at a preselected distance from image sensor 31 to focus light entering through the distal end of illumination and camera module 11 onto image sensor 31.

Image sensor 31 preferably comprises a CMOS image sensor such as are commonly used to provide camera functionality in smartphones and medical applications. Such image sensors are available from a number of manufacturers, and include, for example, the OV6930 available from Omnivision Technologies, Inc., Santa Clara, Calif. In one embodiment, the image sensor has a resolution of 400×400 pixels when operated at 30 frames per second, operates in a low light setting, and includes the processing circuitry to output an analog signal. The image sensor may be paired with lens 34 selected to provide a field of view of 120 degrees.

Processor board 14 and camera board and frame grabber 15 may be conventional components configured for processing the output of the image sensor to provide a real-time video image of the work area under examination. In one embodiment, the image sensor detachably coupled to the processor board by a thin cable with 9 wires, which receives analog signals from the image sensor and converts those signals to digital signals. Frame grabber 15 may be embedded as part of processor board 14, which is in turn connected to computer 18 and display 19a or 19b via cable 17 or wireless connection 17'. If wireless connection 17' is employed, it is possible to have a display fixed at a stand, such as an iPad or iPad Mini tablet computer, both available from Apple Computer, Inc., Cupertino, Calif. which can in turn transmit the images anywhere in the world for viewing by a specialist.

Some of the imaging components of illumination and camera module 11 may be provided as part of a preconfigured camera module supplied by the image sensor manufacturer, e.g., the OV6930 image sensor module described above, which includes automatic gain control, automatic exposure control or white balance capabilities, or these functions may be supplied by additional components. Preferably, the image sensor is made using a CMOS process that enables an extremely small footprint. For example, the image sensor of the OV6930 image sensor module has a diameter of only 2.55 mm. In addition, the camera board may be disposed in housing 13, as depicted in FIG. 1, in which case, the length of the illumination and camera module may be reduced from 6 mm to as low as 3 mm.

Depending upon the intended application of endoscope 10, processor board 14 may include memory for directing storage of video images to computer 18, or may include software for processing the outputs of several image sensors to provide two-dimensional or three-dimensional reconstructions of the body lumen being examined for display on optional displays 19a or 19b. Because the image sensor preferably is configured to work in a low light setting, the illumination provided by LEDs 27 may be turned off using switches 20 located on housing 13 if there is sufficient ambient light for the image sensor to function.

In one preferred embodiment, processor board 20 or computer 18 may be programmed to display not only a real-time video image of work area presently within the field of view of the image sensor, but also may display a graphical user interface that showing a two- or three-dimensional reconstruction of the body lumen including a virtual image of the distal end of the endoscope. In this manner, the physician is provided not only the current view seen by the image sensor, but also an indication of the location of the distal tip of the endoscope in relation to the length of the body lumen travelled during movement of the distal tip.

As a further alternative embodiment, endoscope 10 may be provided with a modular capability. For example, although image sensor 31 of the embodiment of FIGS. 1 and 2 is described as couple to wires 32 in cable 12, this coupling may be detachable to permit image sensors having different fields of view or lenses with different magnifications to be assembled into illumination and camera module 11 by the physician or assistant prior to use, thereby allowing endoscope 10 to be tailored to the specific patient and intended application. In this case, the illumination and camera components of illumination and camera module 11 may be supplied by the manufacturer to the physician or hospital in separate sterile packages, and then assembled in a sterile environment prior to use.

Figure 3:
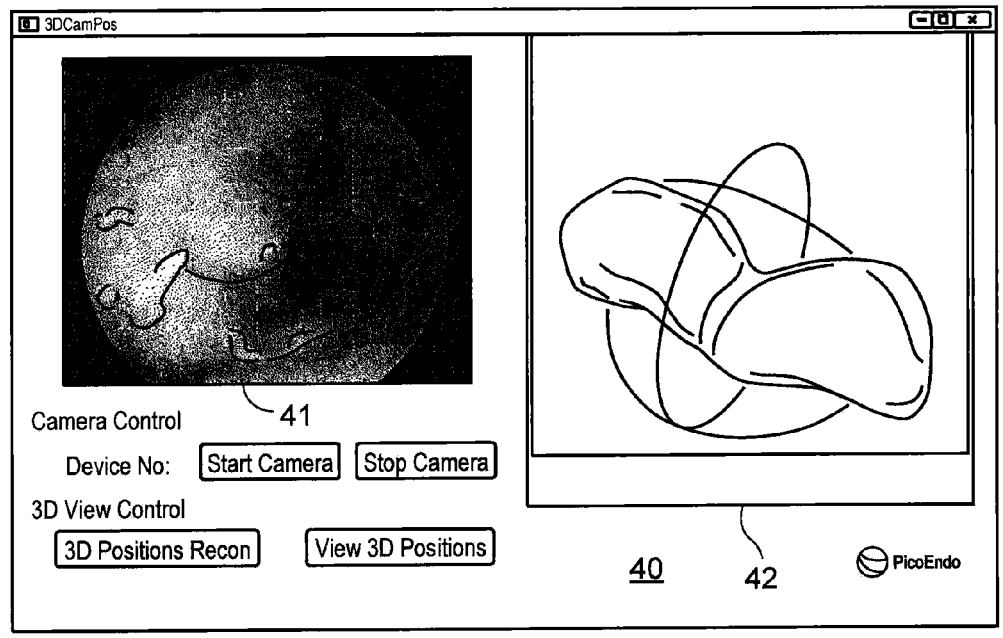
FIG. 3 is a representative screen-shot of a display depicting a real-time video image generated using the endoscope of the present invention a three-dimensional reconstruction of a constriction observed in a body lumen.
Figure 4:
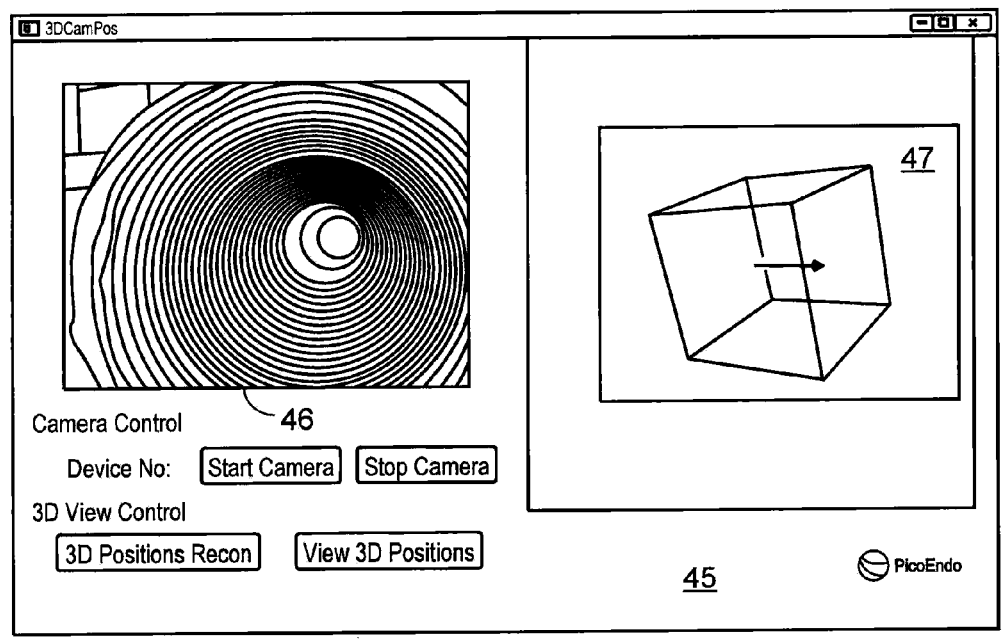
FIG. 4 is a representative screen-shot of a display showing a schematic view of the distal tip of the endoscope as it is advanced through a simulated body lumen.

Referring now to FIGS. 3 and 4, representative screenshots such as may be generated by processor board 14 and displayed on displays 19*a* and 19*b* are described. Processor board 14 or computer 18 may be programmed to provide customized user interface 40 that displays video images captured in real time, such as still image 41 on the left-hand side of FIG. 3, as well as three-dimensional reconstruction of the lumen 42, on the right-hand side, based on analyzing the lumen diameter as the distal end of the endoscope is advanced through the organ. Here it is possible to see the lumen from different angles by rotating the object using an input device associated with the display.

FIG. 4 is a representative screen shot of display 45 showing, on the left hand side, series of overlapping still images 46 captured during advancement of the distal end of the endoscope through a simulated body lumen, while on the right hand side virtual image 47 is depicted showing orientation of the distal end of the endoscope as it travels through the lumen.

Figure 5:
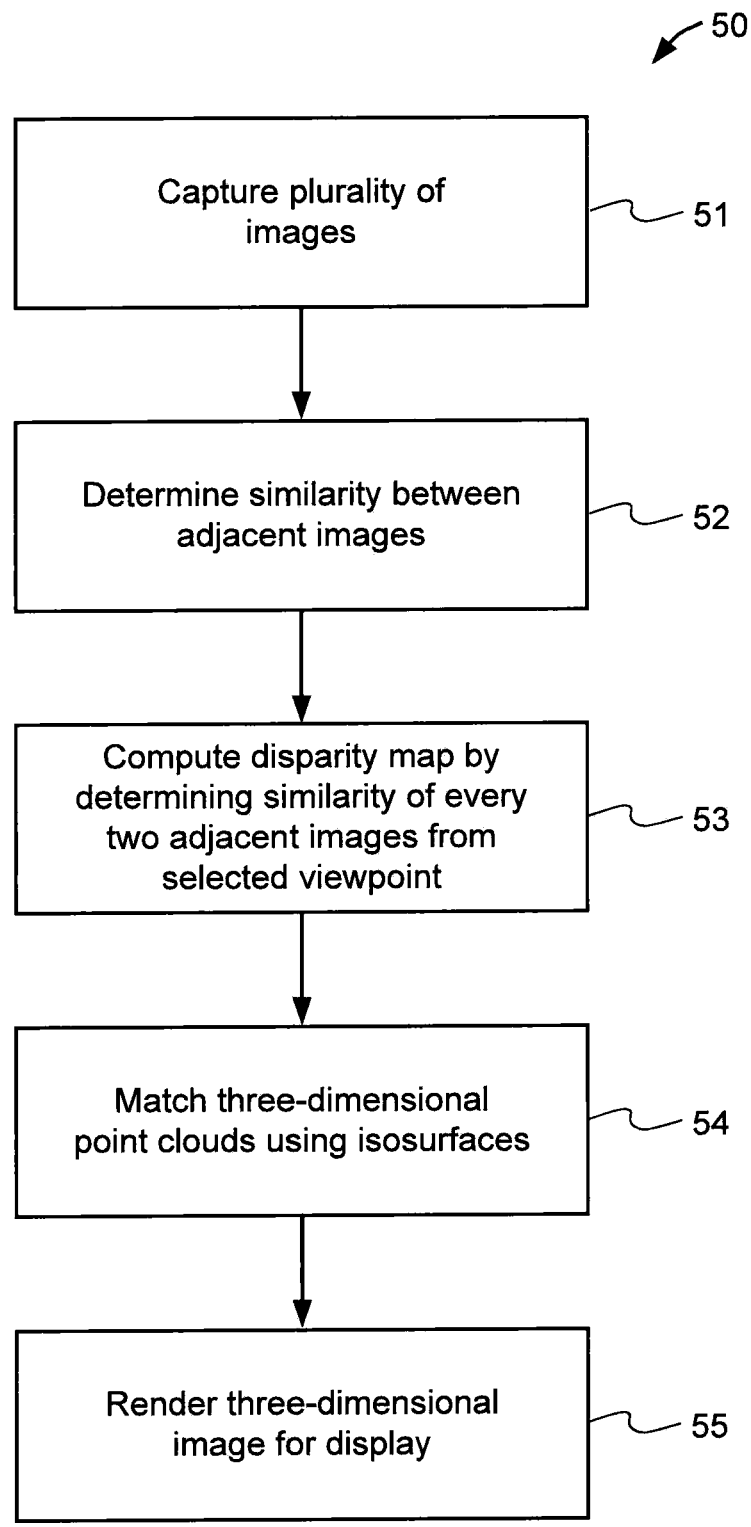
FIG. 5 is a flow diagram describing a process of generating three-dimensional reconstructions of body features using a plurality of still images.

Generation of three-dimensional reconstructions may be performed by using method 50 described with respect to FIG. 5. First, at step 51, a plurality of still images are captured and stored in memory. Next, as step 52, similarity between adjacent images is measured using a search to determine correspondence of points on adjacent images. This serves as a calibration feature that confirms that adjacent points may be represented by a smooth surface in the reconstruction rendering. At step 53, a disparity map is generated by creating for each two adjacent images a depth map corresponding to a particular viewpoint. This viewpoint may be either one of the view points of the input images, or may be a viewpoint corresponding to a completely different virtual position. Then, at step 54, three-dimensional point clouds are matched using and isosurface approach. In particular, an estimate is generated for each pair of three-dimensional point clouds, and a rigid transformation is selected that relates the two if they are determined to be reasonably similar. By matching every adjacent set of point clouds, it is possible to generate a three-dimensional rendering of the viewed image, which then may be displayed, at step 55, as depicted as reconstruction 42 of FIG. 3.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

What is claimed is:

1. A single-use, disposable illumination and camera module for an endoscope comprising:
    a cable configured for insertion in a lumen of a body, the cable having a proximal end configured to be removably connected to endoscope circuitry and a distal region;
    an annular light diffuser disposed on the distal region of the cable, the annular light diffuser having a proximal end, a distal end, a length of 6.0 mm or less, and a diameter of 5.0 mm or less, the distal end having a curved cross-section, the annular light diffuser comprising an optically transparent material;
    a camera having an image sensor and a lens having a field of view, the image sensor disposed concentrically within the annular light diffuser; and
    at least one light emitting diode optically coupled to the proximal end of the annular light diffuser,
    wherein light emitted by the light emitting diode is projected through the curved-cross section of the distal end of the annular light diffuser to provide substantially uniform illumination within the field of view of the lens when disposed and activated within the lumen of the body.

2. The single-use, disposable illumination and camera module of claim 1, wherein the curved cross-section comprises an arc of a circle or an ellipse.

3. The single-use, disposable illumination and camera module of claim 1, further comprising a reflective coating disposed on one of an interior surface of the annular light diffuser or an exterior surface of the light diffuser.

4. The single-use, disposable illumination and camera module of claim 1, wherein the camera comprises a CMOS camera.

5. The single-use, disposable illumination and camera module of claim 1, wherein the image sensor and lens are disposed within a light shield.

6. The single-use, disposable illumination and camera module of claim 1, wherein the camera comprises an array of at least 400×400 pixels.

7. The single-use, disposable illumination and camera module of claim 1, wherein the annular light diffuser comprises polycarbonate.

8. The single-use, disposable illumination and camera module of claim 1, wherein the field of view of the lens comprises at least 45 degrees.

9. The single-use, disposable illumination and camera module of claim 1, wherein the lens comprises a chromatically correcting coating.

10. The single-use, disposable illumination and camera module of claim 1, wherein the light emitting diode is coupled to the proximal end of the annular light diffuser with a glue having a desired transmissivity for a predetermined range of wavelengths.

11. An apparatus for imaging an inner surface of a lumen in a body, comprising:
    a single-use, disposable capsule housing that is sized to readily pass through the lumen, the single-use, disposable capsule housing having a camera having an image detector and a lens, an optically transparent annular light diffuser having a proximal end, a distal end, a length of 6.0 mm or less, and a diameter of 5.0 mm or less, and a light source coupled to the proximal end of the annular light diffuser, wherein light emitted by the light source is projected through the distal end of the annular light diffuser having a curvature to provide substantially uniform illumination within a field of view of the lens when disposed within and activated in the lumen of the body, and wherein the image detector is disposed concentrically within the annular light diffuser; and a flexible tether detachably connected to the single-use, disposable capsule housing, the flexible tether configured to extend proximally through a lumen to enable a force to be applied to the single-use, disposable capsule housing to control a movement of the single-use, disposable capsule housing within the lumen, and to permit retraction of the single-use, disposable capsule housing from the lumen.

12. The apparatus of claim 11, wherein the curvature comprises an arc of a circle or an ellipse.

13. The apparatus of claim 11, wherein the single-use, disposable capsule housing further comprises a reflective coating disposed on an interior surface of the annular light diffuser.

14. The apparatus of claim 11, wherein the image sensor comprises a CMOS image sensor.

15. The apparatus of claim 11, wherein the image sensor and lens are disposed within a light shield.

16. The apparatus of claim 11, wherein the tether includes at least one electrical lead that is coupled to the camera and conveys an electrical signal from the camera to a location that is outside of a lumen in a body.

17. The apparatus of claim 11, wherein the single-use, disposable capsule housing is sized and configured to be swallowed by a patient with the tether connected thereto and the tether includes a plurality of scale markings that serve to enable a user to measure a distance traveled by the single-use, disposable capsule housing into a lumen of a body.

18. The apparatus of claim 11, wherein the light source comprises at least one light emitting diode.

19. The apparatus of claim 11, further comprising a wireless chipset configured to wirelessly transmit video images output by the camera to a display.

20. The apparatus of claim 11, further comprising a processor programmed with software that accepts as input a plurality of still images generated by the camera and outputs for display a three-dimensional rendering of a body feature based on the plurality of still images.

* * * * *